US00PP27807P3

(12) United States Plant Patent
Stemkens

(10) Patent No.: US PP27,807 P3
(45) Date of Patent: Mar. 21, 2017

(54) ***GAILLARDIA* PLANT NAMED 'GAIZ0005'**

(50) Latin Name: *Gaillardia aristata*
Varietal Denomination: GAIZ0005

(71) Applicant: SYNGENTA PARTICIPATIONS AG, Basel (CH)

(72) Inventor: Henricus Godefridus Wilhelmus Stemkens, Enkuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/757,305

(22) Filed: Dec. 15, 2015

(65) Prior Publication Data

US 2016/0198616 P1 Jul. 7, 2016

Related U.S. Application Data

(60) Provisional application No. 62/100,124, filed on Jan. 6, 2015.

(51) Int. Cl.
*A01H 5/02* (2006.01)

(52) U.S. Cl.
USPC ..... Plt./431

(58) Field of Classification Search
USPC ..... Plt./431
CPC ..... A01H 5/025
See application file for complete search history.

*Primary Examiner* — Kent L Bell
(74) *Attorney, Agent, or Firm* — Dale Skalla

(57) ABSTRACT

A new *Gaillardia* plant named 'GAIZ0005' particularly distinguished by the compact and semi-upright plant habit and the large bi-color inflorescences of a striking red and yellow color.

1 Drawing Sheet

Latin name of the genus and species of the plant claimed: *Gaillardia aristata.*

Varietal denomination: 'GAIZ0005'.

BACKGROUND OF THE NEW PLANT

The present invention comprises a *Gaillardia* plant, botanically known as *Gaillardia aristata*, and hereinafter referred to by the variety name 'GAIZ0005'.

'GAIZ0005' is a product of a planned breeding program. The new cultivar has large bicolor inflorescences of a striking red and yellow color in combination with compact and semi-upright plant habit.

'GAIZ0005' originated from an open pollination occurring in the summer of 2007 in a controlled environment in Enkhuizen, Netherlands. The female parent was an unpatented plant identified as 'D2674', having yellow and red, bi-color inflorescences and a more vigorous and more upright plant habit than 'GAIZ0005'.

The male parent is unknown, because this was an open pollination with a cloud of pollen from the whole population.

The resulting seeds were sown in Enkhuizen, Netherlands in March 2008. 'GAIZ0005' was selected as one flowering plant designated 'L5624-12' within the progeny of the stated cross in July 2008.

The first act of asexual reproduction of 'GAIZ0005' was accomplished when vegetative cuttings were propagated from the initial selection in October 2008 in a controlled environment in Enkhuizen, Netherlands.

BRIEF SUMMARY OF THE INVENTION

Horticultural examination of plants grown from cuttings of the plant initiated in the spring of 2009 in Enkhuizen, Netherlands, and continuing thereafter, has demonstrated that the combination of characteristics as herein disclosed for 'GAIZ0005' are firmly fixed and are retained through successive generations of asexual reproduction.

'GAIZ0005' has not been observed under all possible environmental conditions. The phenotype may vary significantly with variations in environment such as temperature, light intensity, and day length.

Plant Breeder's Rights for this cultivar have been applied for with the European Community Plant Variety Office (CPVO) on Jan. 10, 2014, No. 2014/0068 and in Canada on Jul. 2, 2014, No. 14-8380. 'GAIZ0005' has not been made publicly available more than one year prior to the filing of this application.

The following traits have been repeatedly observed and are determined to be basic characteristics of the new variety. The combination of these characteristics distinguishes this *Gaillardia* as a new and distinct variety.

BRIEF DESCRIPTION OF THE PHOTOGRAPHS

The accompanying photographic drawing shows typical inflorescence and foliage characteristics of 'GAIZ0005' with colors being as true as possible with an illustration of this type.

Figure 1:
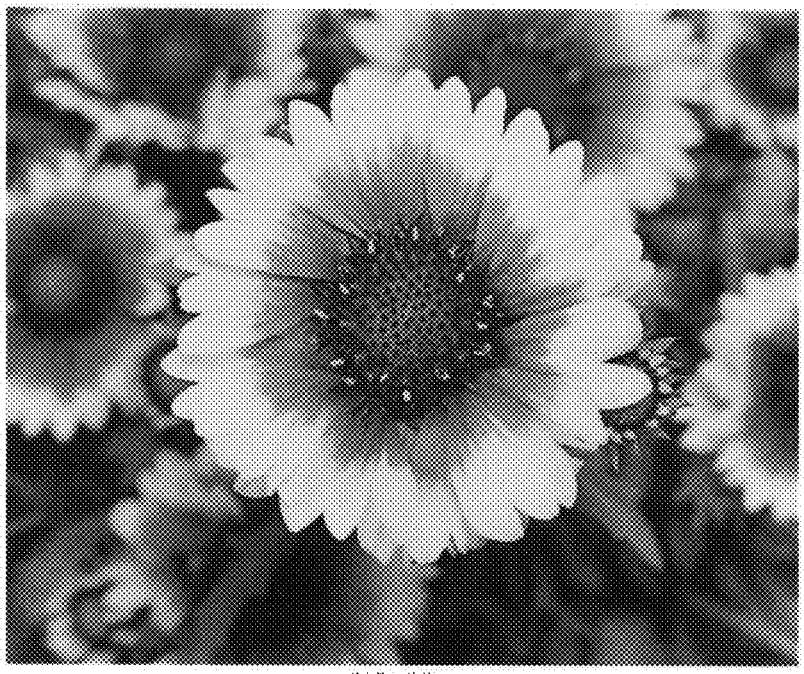
Figure 2:
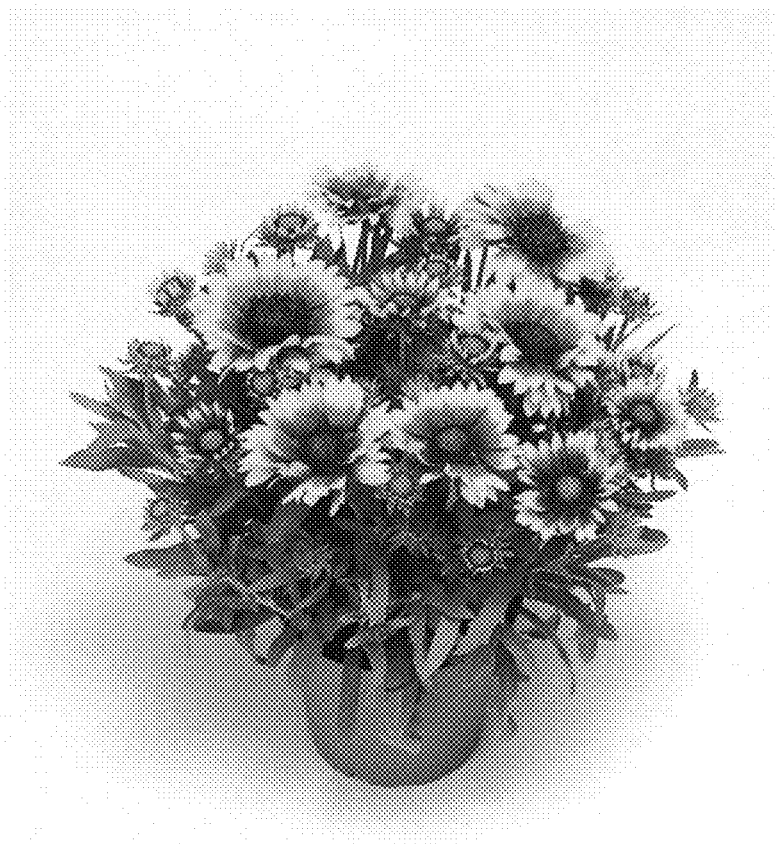

The photographic drawing shows in FIG. 1 a close-up of the inflorescence and in FIG. 2 a whole flowering plant of the new variety.

DETAILED BOTANICAL DESCRIPTION

The aforementioned photographs were taken on July 2012, from plants grown in an outdoor trial in Enkhuizen, Netherlands. These plants were grown in 13 cm pots and were approximately 3 months old.

The plant descriptions and measurements were taken in Enkhuizen, Netherlands on Aug. 15, 2014 using 12-13 week-old plants from an outdoor trial field. The cultivation of these plants had started in early June 2014 with planting rooted cuttings into 13 cm pots and growing them on the ground under natural outdoor conditions through the summer months.

Color references are made to The Royal Horticultural Society Colour Chart (R.H.S.) 2001

DIFFERENCES BETWEEN THE NEW VARIETY 'GAIZ0005' AND A SIMILAR VARIETY

| | 'GAIZ0005' | 'Gallo Dark Bicolor' |
|---|---|---|
| Inflorescence, diameter: | 10 cm | 8 cm |
| Flower color: | RHS 185A, around the center, and yellow: RHS 17A for the outer half | RHS 179A, with yellow tips: RHS 17B |
| Bud color: | Green with dark edges | Green |

Plant:

*Type*.—Perennial, herbaceous, continuously flowering through the summer months, vernalization not essential for initiating of flowering, hardiness tolerates temperature above minus 10° centigrade (frost).

*Form, growth and habit*.—Upright, tight and well-branched habit, relatively compact and small in size with the inflorescence heads only a little above the foliage canopy.

*Plant height* (*without inflorescences*).—10-12 cm.

*Plant height* (*inflorescence included*).—20.5 cm.

*Plant width*.—25.0 cm.

Roots:

*Number of days to initiate and develop roots*.—21-25 days at about 22 degrees C.

*Type*.—Fine, fibrous, free branching.

*Color*.—RHS N155B but whiter.

Foliage:

*Arrangement*.—Alternate, simple leaves.

*Immature, leaf color, upper surface*.—RHS 138A.

*Lower surface*.—RHS 138B.

*Mature, leaf color, upper surface*.—147A to RHS 147B.

*Lower surface*.—147A to RHS 147B.

*Length*.—6.3-7.5 cm.

*Width*.—1.0-1.2 cm.

*Shape*.—Lanceolate to linear, basal leaves might have some lobes (3-4).

*Base shape*.—Attenuate.

*Apex shape*.—Acute.

*Margin*.—Mainly entire; basal leaves may develop a few lobes.

*Texture, both surfaces*.—Canescent hair, lying on the surface, with a few longer, upright hairs along the margins and the midrib of the lower surface.

*Color of veins, upper surface*.—From RHS 144A, near base, to RHS 146B.

*Color of veins, lower surface*.—RHS 144A near base; becoming indistinct towards tip.

*Petiole*.—Sessile, no petiole.

Stem:

*Quantity of main branches per plant*.—15, each with 1 to 4 secondary branches.

*Color of stem*.—From RHS 144A to RHS 144B.

*Stem length*.—About 10.0 cm.

*Stem diameter* (*at mid portion*).—0.4 cm.

*Length of internodes* (*at mid portion*).—1.5-2.5 cm mostly.

*Texture*.—Pilose hair of medium density.

Peduncle:

*Color of peduncle*.—RHS 144B.

*Length of peduncle*.—About 6.0-8.0 cm.

*Peduncle diameter*.—0.25-0.3 cm.

*Texture*.—Covered with very fine pubescence and with single longer hairs.

Inflorescence:

*Type*.—Capitulum (compositae-type), single inflorescences, borne terminally on short peduncles above the foliage.

*Quantity of inflorescences per plant*.—About 60 flower heads and buds.

*Lastingness of individual blooms on the plant*.—About two weeks depending on temperature.

*Fragrance*.—None.

Bud (just when opening/showing color):

*Color*.—RHS 7B and RHS 143C.

*Length*.—1-1.2 cm.

*Width*.—1.2-1.5 cm.

*Shape*.—Cup-shaped.

*Texture*.—Covered with fine pubescence and with long hair at the edges of the phyllaries.

Young inflorescence:

*Diameter*.—About 3.2-3.5 cm.

*Color of rays*.—Approximately RHS 46A with a yellow ring, near RHS 14B.

*Color of rays, lower side*.—From RHS 13B and RHS 46B.

*Color of disc with the disc florets still closed*.—Near RHS 187B and RHS N144A.

Mature inflorescence:

*Shape*.—Medium sized, daisy-type inflorescences with two whorls of ray florets surrounding the disk, and more or less horizontally directed.

*Diameter of whole inflorescence*.—10 cm.

*Diameter of disc*.—2.3-2.5 cm.

*Diameter of receptacle*.—About 3.8 cm.

Ray florets:

*Average quantity of rays*.—11-16, in one to two whorls.

*Color upper surface*.—Basal half RHS 46A; distal half RHS 14B.

*Color of lower surface*.—RHS 46B near base; RHS 13B near tip.

*Length*.—3 cm.

*Width*.—1.5 cm.

*Shape*.—Ligulate to weakly oblanceolate.

*Apex shape*.—Obtuse.

*Margin*.—Entire.

*Texture, upper surface*.—Glabrous.

*Texture, lower surface*.—Uniformly fine pubescence, slightly protruding veins.

Disc florets:

*Average quantity of disc florets*.—About 80.

*Shape*.—Tube-shaped.

*Apex shape*.—5-pointed with acute tips.

*Color of young disk florets* (*just before opening*), *at apex*.—RHS 187B, purple red.

*Color of open floret*.—RHS 187A, corolla of RHS 187D.

*Length of floret*.—1.1 cm.

*Width at apex.*—0.4 cm.

Involucre/receptacle:

*Shape.*—Flattened semi-sphere, formed by the phyllaries in an overlapping arrangement.

*Diameter (width).*—3.8 cm.

*Diameter (depth).*—1.5 cm.

Phyllaries:

*Quantity of phyllaries.*—35.

*Shape.*—Lanceolate.

*Apex shape.*—Acuminate.

*Base.*—Sessile, fused with receptacle.

*Margins.*—Entire.

*Color, outer surface.*—RHS 147B.

*Color, inner side.*—RHS 147B.

*Length.*—1.6 cm.

*Width.*—0.5 cm.

*Texture outer surface.*—Densely pubescent with some longer hair, mostly at the edges.

*Texture inner surface.*—Same as outer surface.

Reproductive organs:

*Gynoecium.*—Developed in disc florets.

*Pistil, number per floret.*—One.

*Pistil, length.*—1.2 cm.

*Style color.*—RHS 12A.

*Style length.*—0.5 cm.

*Stigma color.*—RHS 187A.

*Stigma shape.*—Bi-lobed.

*Stigma, length.*—0.7 cm.

*Ovary, length.*—0.1 cm.

*Androecium.*—Present in disc florets only.

*Number of stamen.*—4 per floret, tube.

*Filaments.*—Free filaments, united anthers.

*Anther, shape.*—Linear, 4 mm in length.

*Anther color.*—RHS 157D at base, rest is RHS 17C.

*Pollen amount.*—Moderate.

*Color of pollen.*—RHS 17B.

*Fertility/seed set.*—Has not been observed on this hybrid.

*Disease/pest resistance.*—Has not been observed on this hybrid.

What is claimed is:

1. A new and distinct variety of *Gaillardia* plant named 'GAIZ0005' substantially as illustrated and described herein.

* * * * *